United States Patent
Senaratne et al.

(10) Patent No.: US 10,337,074 B2
(45) Date of Patent: *Jul. 2, 2019

(54) METHOD OF OPERATION OF FERMENTATION OF CARBON MONOXIDE AND HYDROGEN CONTAINING GASEOUS SUBSTRATE

(76) Inventors: Ryan Senaratne, Fayetteville, AR (US); Syrona Scott, Fayetteville, AR (US); Ching-Whan Ko, Fayetteville, AR (US)

(*) Notice: Subject to any disclaimer, the term of this patent is extended or adjusted under 35 U.S.C. 154(b) by 290 days.

This patent is subject to a terminal disclaimer.

(21) Appl. No.: 13/989,102

(22) PCT Filed: Nov. 14, 2011

(86) PCT No.: PCT/US2011/001901
§ 371 (c)(1),
(2), (4) Date: May 23, 2013

(87) PCT Pub. No.: WO2012/074544
PCT Pub. Date: Jun. 7, 2012

(65) Prior Publication Data
US 2013/0244220 A1    Sep. 19, 2013

Related U.S. Application Data

(60) Provisional application No. 61/458,899, filed on Dec. 3, 2010.

(51) Int. Cl.
*C12Q 3/00* (2006.01)
*C12P 7/06* (2006.01)
(Continued)

(52) U.S. Cl.
CPC .............. *C12Q 3/00* (2013.01); *C12M 21/04* (2013.01); *C12M 27/02* (2013.01); *C12M 29/04* (2013.01);
(Continued)

(58) Field of Classification Search
None
See application file for complete search history.

(56) References Cited

U.S. PATENT DOCUMENTS 4,351,905 A    9/1982 Clyde
4,393,136 A    7/1983 Cheetham
(Continued)

FOREIGN PATENT DOCUMENTS

WO    WO 98/00558    1/1998
WO    WO 00/68407    11/2000

OTHER PUBLICATIONS

Abrini, J., Naveau etc. Clostridium autoethanogenum, Spenov, an Anaerobic Bacterium That Produces Ethanol from Carbon-Monoxide, Archives of Microbiology, 1994, 161(4), 345-51.
(Continued)

*Primary Examiner* — Erin M. Bowers
(74) *Attorney, Agent, or Firm* — James P. Krueger

(57) ABSTRACT

A method of gaseous substrate fermentation comprising: adding gaseous substrate comprising carbon monoxide (CO) and hydrogen ($H_2$) into an aqueous medium in a bioreactor; said method comprising measuring conversion of CO; measuring conversion of $H_2$; increasing flow of gaseous substrate by a preselected flow factor; wherein agitation comprises greater than or equal to target agitation rate.

9 Claims, 1 Drawing Sheet

(51) Int. Cl.
    C12M 1/107    (2006.01)
    C12M 1/06     (2006.01)
    C12M 1/00     (2006.01)
(52) U.S. Cl.
    CPC ............ *C12M 29/18* (2013.01); *C12P 7/065* (2013.01); *Y02E 50/17* (2013.01)

(56) References Cited

U.S. PATENT DOCUMENTS

| | | | |
|---|---|---|---|
| 4,400,470 | A | 8/1983 | Zeikus |
| 4,654,123 | A | 3/1987 | Berg |
| 4,737,459 | A | 4/1988 | Zeikus |
| 4,886,751 | A | 12/1989 | Thorsson |
| 5,173,429 | A | 12/1992 | Gaddy |
| 5,182,199 | A | 1/1993 | Hartley |
| 5,593,886 | A | 1/1997 | Gaddy |
| 5,807,722 | A | 9/1998 | Gaddy |
| 5,821,111 | A | 10/1998 | Gaddy |
| 6,136,577 | A | 10/2000 | Gaddy |
| 6,340,581 | B1 | 1/2002 | Gaddy |
| 6,919,488 | B2 | 7/2005 | Melnichuk |
| 7,285,402 | B2 * | 10/2007 | Gaddy .................. C12P 7/065 435/140 |
| 2012/0088282 | A1 | 4/2012 | Gaddy |

OTHER PUBLICATIONS

Bahl, et al "Continuous Production of Acetone and Butonol by Clostridium acetoutylicum in a Two-Stage Phosphate Limited Chemostat" Appl. Microbiol. Biotechnol 09-96;46:176-182.

Bahl, et al. "Nutritional Factors Affecting the Ratio of Solvents Produced by Clostridium acetobutylicum" Appl. Environ. Microbiol. (07-86) 52(1):169-172.

Barik et al. "Biological Production of Alcohols from Coal through Indirect Liquefaction" Appl. Biochem. Biotechnol. Proc of the 9th Symp on Biotechnol. for Fuels (1988) 18:363.

Bredwell, M.D. Srivastava et al. "Reactor Design Issues for Synthesis-Gas Fermentations" Biotechnol Prog. (1999) 15, 834-844.

Bryant et al. "Buffering as a Means for Increasing Growth and Butanol Production by Clostridium acetobutylicum" J. Indust Microbiol (02-88) 3:45:55.

Byung Hong Kim, P.B et al. "Control of Carbon & Electron Flow in Clostridium acetobutylicum Fermentations: Utilization of Carbon Monoxide to Inhibit Hydrogen Production and to Enhance Butanol Yields;" Applied Environmental Microbiology; (1984) 48 (4), 764-770.

Chang, I.S. et al. Formulation of Defined Media for Carbon monoxide Fermentation by Eubacterium limosum KIST612 and the growth Characteristics of the Bacterium Journal of Bioscience and Bioengineering, (1999) 88(6), 682-685.

Clarke et al "Nature and Significance of Oscillatory Behaviour during Solvent Productioin by Clostridium acetobuylicum in Continuous Culture" 1987 Biotec Bioengin 32:538-544.

Degraef et al. "The Steady-State Internal redox State (NADH/NAD) Reflects the External Redox State and is Correlated with Catabolic Adaptation in *Escherichia coli*" J. Bacteriol, (Apr. 1999)181(8): 2351-2357.

Diekert, G. et al. "Metabolism of Homoacetogens" Antonie Van Leeuwenhoek International Journal of General and Molecular Microbiology, (1994) 66(1-3), 2009-221.

Ferras et al "Acetonobutylic Fermentation: Improvement of Performances by Coupling Continuous Fermentation and Ultrafiltration" Biotechnol. Bioengin (Jun. 1985) 28:523.

Girbal, L. et al. Regulation of Metabolic Shifts in Clostridium Acetobutylicum ATCC 824 FEMS Microbiology Reviews (1995) 17(3) 287-297.

Gottschal, J.C. et al. The Induction of Acetone and Butanol Production in Cultures of Clostridium-Acetobutylicum by Elevated Concentrations of Acetate and Butyrate, FEMS Microbiology Letters (1981) 12 (4) 385-389.

Gottwald et al. "The Internal pH of Clostridium acetobutylicum and its Effect on the Shift from Acid to Solvent Formation" Arch. Microbiol (Oct. 1985) 143:42-46.

Grahame et al. "Substrate and Cofactor Reactivity of a Carbon Monoxide Dehyrogenase-Corrinoid Enzyme Complex: Stepwise Reduction of Iron-Sulfur and Corrinoid Centers, the Corrinoid CO2 +/1+ Redox Midpoint Potential, and Overall Synthesis of Acetyl-COA" Biochem, (Oct. 12, 1993) 32:10786-93.

Guedon et al. "Carbon and Electron Flow in Clostridium cellulolyticum Grown in Chemostat on Synthetic Medium" J. Bacteriol (May 1999) 181 (10): 3262-3269.

Hansen, J.B. "High Conversion of Synthesis Gas into Oxygenates" Studies in Surface Science and Catalysis (1997) 61, 457-67.

Hols et al. "Acetate utilization in Lactococcus Lactis Deficient in Dehydrogenase: A Rescue Pathway for Maintaining Redox Balance" J. Bacteriol (Sep. 1999) 181 (17): 5521.

Huseman et al. "Solventogenesis in Clostridium acetobutylicum Fermentations related to Carboxylic Acid and Proton Concnetrations" Biotechnol Bioengin (Sep. 1988) 32:843-52.

Ingram et al. "Expression of Different Levels of Ethanologenic Enzymes from Zymomonas mobilis in Recombinant Strains of *Escherichia coli*" Appl. Environ. Microbiol (Feb. 1988) 54(2): 397-404.

Jung, G.Y.et al. "Isolation and Chracterization Rhodopseudomonas palustris P4 which utilizes CO with the production of H2" Biotechnology Letters (1999) 21(6) 525-529.

Kim et al. "Redox Potential in Acetone-Butanol Fermentations" 9th Symposium on Biotechnology for Fuels and Chemicals, Boulder Co (May 1987).

Kim et al. "Electron Flow Shift in Clostridium acetobutylicum Fermentation by Electrochemically Introduced Reducing Equivalent" Biotechnol Lett (Feb. 1988) 10(2): 123-128.

Klasson, K.T. et al. "Kinetics of Light Limited Growth and Biological Hydrogen-Production from Carbon-Mnoxide and Water" Rhodospirillum-Rubrum Journal of Biotech (1993) 29(1-2), 177-188.

Klasson, K.T. et al. "Bioconversion of Synthesis Gas into Liquid or Gaseous Fuels" Enzyme and Microbial Technology (1992) 14(8) 602-608.

Klasson, K.T. "Biological conversion of Coal and Coal-Derived Synthesis Gas" Fuel (1993) 72(12), 1673-1678.

Klier, K "Methanol Synthesis" Advances in Catalysis (1982) Advances in Catalysis 31.

Krasna, A.I. et al. "The Inhibition of Hydrogenase by Nitric Oxide" Proceedings of the National Academy of Sciences (1954) 40(4), 225-227.

Krasna, A.I. "Hydrogenase: Properties and Application" Enzyme and Microbial Technology (1979) 1(3), 165-172.

Kutzenok, A. et al. "Degenerative Processes in a Strain of Clostridium Butylicum" Journal of Bacteriology (1952) 64(6), 829-836.

Landuyt et al. "Transition from Acid Fermentation to Solvent Fermentation in a Continuous Dilution Culture of Clostridium Thermosaccharolyticurn" Annals of NY Acdy of Sciences (12-2987), 473-478.

Lemon, B.J. et al, Binding of Exogenously added Carbon Monoxide at the Active Site of the iron-only Hydrogenase (Cpl) from Clostridium pasteurianum, Biochemistry (1999) 38(40), 12969-12973.

Liou et al. "*Clostridium Carboxidivorans* sp. nov., a Solvent-Producing Clostridium Isolated from an Agricultural Settling Lagoon, and Reclassification of the Acetogen Clostridium Scatologenes Strain SL1 as *Clostridium Drakei* sp. nov." Int. J. Sys. Evol. (Sep. 2005) Microbiol 55:2085-2091.

Ljungdahl, L.G. "The Autotrophic Pathway of Acetate Synthesis in Acetogenic Bacteria" Annual Rev of Microbiology (1986) 40, 415-450.

Long, et al. "Sporulation of Clostridium acetobutylicum P262 in a Defined Medium" Appl. Environ. Microbiol (Apr. 1983) 45(4):1389-1393.

Lovitt et al. "Ethanol Production by Thermophilic Bacteria: Biochemical Basis for Ethanol and Hydrogen Tolerance in Clostridum thermohydrosulfuricum" J. Bacteriol (06-88) 170(6):2809.

Lynd et al. "Thermophilic Ethanol Production" Appl. Biochem Biotech (1991) 28/29:549.

(56) References Cited

OTHER PUBLICATIONS

Martin et al. "Effects of Acetic and Butyric Acids on Solvent Production by Clstridium acetobutylicum" Biotech, Lett (Feb. 1983) 5(20):89-94.

Meyer,CL, et al "Increased Levels of ATP and NADH Are Associated with Increased Solvent Production in Continuous Cultures of Clostridium acetobutylicum" Applied Microbiology and Biotechnology, (1989) 30(5) 450-459.

Meyer, C.L. et al. "The Effect of CO on Growth and Product Formation in Batch Cultures of Clostridium acetobutylicum" Biotechnology Letters (1985) 7(1) 37-42.

Meyer, C.L. et al. Carbon Monoxide Gasing Leads to Alcohol Production and Butyrate Uptake without Acetone Formation in Continuous Cultures of Clostridium acetobutylicum Applied Microbiology and Biotechnology (1986) 24(2), 159-167.

Misoph, M. et al. "Effect of $CO_2$ on the fermentation capacities of the acetogen Peptostreptococcus Productus U-1" Journal of Bacteriology (1996) 178(11) 3140-3145.

Murray et al "Ethanol Production by a Newly Isolated Anaerobe, Clostridium saccharolyticum: Effects of Culture Medium and Growth Condiditons" Canad J Microbiol (03-83) 29:342.

Philips et al. "Biological Production of Ethanol from Coal Synthesis Gas medium Development Studies" Appl Biochem Biotech, Proceedings from 14th Symposium on Biotechnology for Fuels and Chemicals (1990) 39/40:559.

Phillips et al. "Synthesis Gas as Substrate for the Biological Production of Fuels and Chemicals" Appl. Biochem. and Biotech, Proceedings of the 15th Symposium on Biotech for Fuels and Chemicals (1994) 45/46:145.

Ram et al. "Ethanol Production by Clostridium thermocellum SS8, A Newly Isolated Thermophilic Bacterium" Biotechnol Lett (Aug. 1989) 11(8):589-592.

Rao, et al. "Manipulation of End Product Distribution in Strict Anaerobes" Annals of NY Academy of Science (Nov. 1987) pp. 76-83.

Rao et al. "Altered Electron Flow in a Reducing Environment in Clostridium acetobutylicum" Biotech Lett (Feb. 1988)10(2):129-132.

Rao et al. "Directed Metabolic Flow with High Butane Yield and Selectivity in Continuous Culture of Clostridium acetobutylicum" Biotech Lett (May 1988) 10(5):313-318.

Rao, et al. "NADH Levels and Solventogenesis in Clostridium-Acetobutylicum-New Insights through Culture Fluorescence" Applied Microbiology & Biotech (1989) 30(1) 59-66.

Reardon et al. "Metabolic Pathway Rates and Culture Fluorescence in Batch Fermentations of Clostridium acetobutylicum" Biotech Prog (Sep. 1987) 3(3) 153-168.

Rothstein et al. "Clostridium thermosaccharolyticum Strain Deficient in Acetate Production" J. Baceriol (Jan. 1986) 165(1):319-320.

Terraciano et al. "Intracellular Conditions Required for Inititation of Solvent Production by clostridium acetobutylicum" Appl. and Environ. Microbiol. (Jul. 1986) 52(1): 86-91.

Tibelius, K.H. et al. Hydrogenase activity in Azospirillum brasilense is inhibited by nitrite, nitric oxide, carbon monoxide and acetylene, Journal of Bacteriology (1984) 160(1), 103-106.

Vega, J. L. et al. "The Biological Production of Ethanol from Synthesis Gas" Applied Biochemistry and Biotech (1989) 20-1, 781-797.

Vega, J. L. et al. "Design of bioreactors for coal synthesis gas fermentations" Resources, Conservation & Recycling (1990) 3(2-3) 149-160.

Vega et al. "The Biological Production of Ethanol from Synthesis Gas" Appl. Biochem. Biotechnol. Proc10th Symp on Biotechnol. for Fuels, Chemicals (1989) 20/21:781.

Wood, H.G., et al. "The Acetyl-CoA Pathway-A Newly Discovered Pathway of Autotrophic Growth" Trends in Biochemical Sciences (1986a); 11(1) 14-18.

Wood, H.G. et al. "The Acetyl-CoA Pathway of Autotrophic Growth" FEMS Microbiology Reviews (1986b) 39(4), 345-362.

Wood, H.G. et al. "A New Pathway of Autotrophic Growth Utilizing Carbon-Monoxide or Carbon-Dioxide and Hydrogen" (1986c) Biochemistry International 12(3), 421-440.

Worden, R.M. et al. "Engineering Issues in Synthesis-Gas Fermentations," 1997 American Chemical Society 18, 320-335.

Girbal, L. et al. "How Neutral Red Modified Carbon & Electron Flow in Clostridium acetobutylicum Grown in Chemostat Culture at Neutral pH" (1995)FEMS Micro. Review 16 151-162.

Examination Report dated Dec. 8, 2003, issued in counterpart European Patent Application No. 01954884.1.

Examiner's Report dated Jul. 29, 2005, issued in counterpart Malaysian Patent Application No. PI20013724.

Kashket, E.R. et al. Clostridial strain degeneration, FEMS Microbiology Reviews (1995); 17(3), 307-315.

Chang, I.S. et al. "CO Fermentation of Eubacterium limosum KIST612" Journal of Microbiology and Biotechnology; 1998; 8(2); 134-140.

Phillips, Klasson, Clausen, Gaddy, "Biological Production of Ethanol from Coal Synthesis Gas-Medium Development Studies" Applied Biochemistry and Biotechnology (1993) 39:40:559.

Ragsdale, S "Enzymology of the Acetyl-CoA Pathway of $CO_2$ Fixation" Critical Reviews in Biochemistry and Molecular Biology, (1991) 26(3/4):261-300.

Taherzadeh et al., "The Effects of Pantothenate Deficiency and Acetate Addition of Anaerobic Batch Fermentation of Glucose by *Saccharomyces cerevisiae*" Appl Microbiol Biotechnol (1996) 46:176-182.

Vasconcelos, I, et al., "Regulation of Carbon and Electron Flow in Clostridium Acetobutylicum Grown in Chemostat Culture at Neutral Ph on Mixtures of Glucose and Glycerol" Journal of Bacteriology (1994) vol. 176, No. 3, 1443-1450.

* cited by examiner

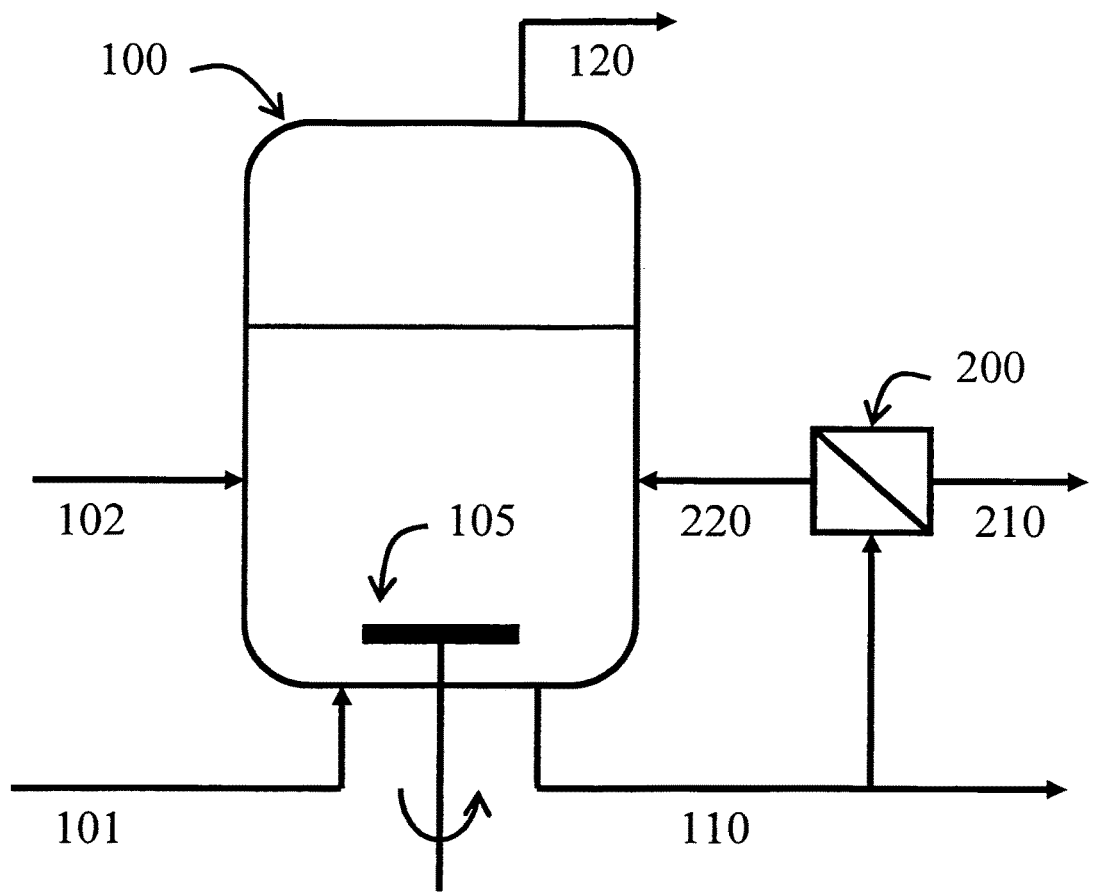

METHOD OF OPERATION OF FERMENTATION OF CARBON MONOXIDE AND HYDROGEN CONTAINING GASEOUS SUBSTRATE

The present disclosure is generally directed to method of fermentation of a gaseous substrate comprising carbon monoxide (CO) and hydrogen ($H_2$). The present disclosure is specifically directed to method of fermentation of a gaseous substrate comprising carbon monoxide (CO) and hydrogen ($H_2$) to produce one or more alcohols.

BACKGROUND

Methods for producing chemicals such as organic acids, e.g. acetic acid and alcohols, e.g. ethanol from microbial fermentation of gaseous substrates comprising carbon monoxide and hydrogen in media containing suitable nutrients and trace minerals using certain bacteria, such as those from the genus *Clostridium*, have been demonstrated. For example, U.S. Pat. No. 5,173,429 to Gaddy et al. discloses *Clostridium ljungdahlii* ATCC No. 49587, an anaerobic microorganism that produces ethanol and acetate from synthesis gas. U.S. Pat. No. 5,807,722 to Gaddy et al. discloses a method and apparatus for converting waste gases into useful products such as organic acids and alcohols using anaerobic bacteria, such as *Clostridium ljungdahlii* ATCC No. 55380. U.S. Pat. No. 6,136,577 to Gaddy et al. discloses a method and apparatus for converting waste gases into useful products such as organic acids and alcohols (particularly ethanol) using anaerobic bacteria, such as *Clostridium ljungdahlii* ATCC Nos. 55988 and 55989.

US Patent Application No. 20070275447 discloses a *clostridium* bacterial species (*Clostridium carboxidivorans*, ATCC BAA-624, "P7") that is capable of synthesizing, from waste gases, products which are useful as biofuel. U.S. Pat. No. 7,704,723 discloses a *clostridium* bacterial species (*Clostridium ragsdalei*, ATCC BAA-622, "P11") that is capable of synthesizing, from waste gases, products which are useful as biofuel.

WO 2007/117157 discloses use of *Clostridium autoethanogenum* (Accession No. DSM 10061, DSMZ, Germany) for the production of ethanol by anaerobic fermentation of substrates containing carbon monoxide. WO 2009/064200 discloses another bacteria (*Clostridium autoethanogenum*, Accession No. DSM 19630, DSMZ, Germany) for the production of ethanol by anaerobic fermentation of substrates containing carbon monoxide.

As described in the art, rate of production of chemicals such as alcohol depend on density of microbial cells ("cell density") in the fermentation medium. Adequately high cell density in the bioreactor is required in order to attain and maintain a high rate of production of chemicals.

U.S. Pat. No. 6,136,577 to Gaddy discloses a process of ethanol production in a fermentation process wherein cell-recycle is used to increase cell density.

U.S. Pat. No. 7,285,402 to Gaddy et al. discloses an anaerobic microbial fermentation process for the production of alcohol wherein a method of increasing cell density is presented during start up using a stock culture wherein there was excess $H_2$ present.

Start-up using a batch inoculum from stock culture ensures a healthy inoculum free from contaminants, but is not always successful as an inoculation procedure because of the rather low cell density employed, especially if the method parameters such as gas rate and agitation rate are pushed upward too rapidly just after inoculation.

Currently, there is a need in the art for improved methods to increase cell density in microbial fermentation of a gaseous substrate. The present disclosure provides a method to increase cell density at a faster rate for microbial fermentation methods of a gaseous substrate.

SUMMARY

The present disclosure provides, as an embodiment, a process of producing one or more alcohols from a gaseous substrate, comprising: fermenting a gaseous substrate comprising carbon monoxide (CO) and hydrogen ($H_2$) in an aqueous medium in a bioreactor; said process comprising measuring conversion of CO; measuring conversion of $H_2$; increasing flow of gaseous substrate by a preselected flow factor in 1.0 to 2.0 range; wherein agitation comprises greater than or equal to target agitation rate; wherein said target agitation rate comprises an agitator speed of 10 to 1000 rpm; wherein comprising increasing flow of gaseous substrate wherein said conversion of CO exceeds a first CO conversion in 25% to 95% range; wherein comprising increasing flow of gaseous substrate wherein conversion of $H_2$ exceeds a first $H_2$ conversion in 25 to 95% range; wherein said bioreactor comprises one or more reactors; wherein said bioreactor comprises cell recycle; wherein adding flow of nutrient medium into bioreactor.

In an embodiment said aqueous medium comprises one or more: biologically pure anaerobic acetogenic microorganism, naturally occurring anaerobic acetogenic microorganism, non-naturally occurring anaerobic acetogenic microorganism, non-naturally occurring anaerobic acetogenic microorganism produced by genetic modification, mutant of naturally occurring anaerobic acetogenic microorganism, mutant of non-naturally occurring anaerobic acetogenic microorganism.

As an embodiment, the present disclosure provides a method of gaseous substrate fermentation comprising: adding gaseous substrate comprising carbon monoxide (CO) and hydrogen ($H_2$) into an aqueous medium in a bioreactor; said method comprising measuring conversion of CO; measuring conversion of $H_2$; increasing flow of gaseous substrate by a preselected flow factor in 1.0 to 2.0 range; wherein difference between conversion of CO and conversion of $H_2$ comprises greater than or equal to a specified conversion difference in 0% to 25% range; wherein comprising increasing flow of gaseous substrate wherein conversion of CO exceeds a first CO conversion in 25 to 95% range; wherein comprising increasing flow of gaseous substrate wherein conversion of $H_2$ exceeds a first $H_2$ conversion in 25 to 95% range.

As an embodiment, the present disclosure provides a method of gaseous substrate fermentation comprising: adding gaseous substrate comprising carbon monoxide (CO) and hydrogen ($H_2$) into an aqueous medium in a bioreactor comprising agitation; said method comprising measuring conversions of CO and $H_2$ and increasing agitation in preselected speed steps; wherein difference of conversions of CO and $H_2$ is less than a specified conversion difference in a range of 0 to 25%; wherein comprising increasing agitation wherein conversion of CO exceeds a second CO conversion in a range of 0 to 25%; wherein comprising increasing agitation wherein conversion of $H_2$ exceeds a second $H_2$ conversion in a range of 0 to 25%.

As an embodiment, the present disclosure provides a method of gaseous substrate fermentation comprising: adding gaseous substrate comprising carbon monoxide (CO) and hydrogen ($H_2$) into an aqueous medium in a bioreactor comprising an agitator; said method comprising measuring conversion of CO; measuring conversion of $H_2$; increasing flow of gaseous substrate by a preselected flow factor in 1.0 to 2.0 range; wherein speed of said agitator comprises greater than or equal to target speed in 10 to 1000 rpm range.

The present disclosure provides a method of gaseous substrate fermentation comprising: adding gaseous substrate comprising carbon monoxide (CO) and hydrogen ($H_2$) into an aqueous medium in a bioreactor; said aqueous medium comprising one or more microorganism; said method comprising measuring conversion of CO; measuring conversion of $H_2$; increasing flow of gaseous substrate by a preselected flow factor in 1.0 to 2.0 range; wherein agitation comprises greater than or equal to target agitation rate; wherein said target agitation rate comprises an agitator speed of 10 to 1000 rpm.

The present disclosure provides a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganism; said method comprising measuring conversion of CO; measuring conversion of $H_2$; increasing flow of gaseous substrate by a preselected flow factor in 1.0 to 2.0 range; wherein speed of said agitator comprises greater than or equal to target speed in 10 to 1000 rpm range.

As an embodiment, the method of the present disclosure comprises increasing flow of gaseous substrate wherein said conversion of CO exceeds a first CO conversion in 25% to 95% range.

As an embodiment, the method of the present disclosure comprises increasing flow of gaseous substrate wherein conversion of $H_2$ exceeds a first $H_2$ conversion in 25 to 95% range.

Further, the present disclosure provides a method of gaseous substrate fermentation comprising: adding gaseous substrate comprising carbon monoxide (CO) and hydrogen ($H_2$) into an aqueous medium in a bioreactor; said aqueous medium comprising one or more microorganism; said method comprising measuring conversion of CO; measuring conversion of $H_2$; increasing flow of gaseous substrate by a preselected flow factor in 1.0 to 2.0 range; wherein difference between conversion of CO and conversion of $H_2$ comprises greater than or equal to a specified conversion difference in 0% to 25% range.

Further, the present disclosure provides, a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganism; said method comprising measuring conversion of CO; measuring conversion of $H_2$; increasing flow of gaseous substrate by a preselected flow factor in 1.0 to 2.0 range; wherein difference between conversion of CO and conversion of $H_2$ comprises greater than or equal to a specified conversion difference in 0% to 25% range.

As an embodiment, the method of the present disclosure comprises increasing flow of gaseous substrate wherein conversion of CO exceeds a first CO conversion in 25 to 95% range.

As an embodiment, the method of the present disclosure comprises increasing flow of gaseous substrate wherein conversion of $H_2$ exceeds a first $H_2$ conversion in 25 to 95% range.

Also, the present disclosure provides a method of gaseous substrate fermentation comprising: adding gaseous substrate comprising carbon monoxide (CO) and hydrogen ($H_2$) into an aqueous medium in a bioreactor comprising agitation; said aqueous medium comprising one or more microorganisms; said method comprising measuring conversions of CO and $H_2$ and increasing agitation in preselected speed steps; wherein difference of conversions of CO and $H_2$ is less than a specified conversion difference in a range of 0 to 25%; comprising increasing agitation wherein conversion of CO exceeds a second CO conversion in a range of 0 to 25%; comprising increasing agitation wherein conversion of $H_2$ exceeds a second $H_2$ conversion in a range of 0 to 25%.

Also, the present disclosure provides, a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing speed of said agitator in preselected speed steps in a range of 0 to 200 rpm; wherein difference of conversions of CO and $H_2$ is less than a specified conversion difference in a range of 0 to 25%.

As an embodiment, the method of the present disclosure comprises increasing speed of said agitator wherein conversion of CO exceeds a second CO conversion in a range of 0 to 25%.

As an embodiment, the method of the present disclosure comprises increasing speed of said agitator wherein conversion of $H_2$ exceeds a second $H_2$ conversion in a range of 0 to 25%.

As an embodiment, said microorganism of the present disclosure comprises one or more of the microorganism including: biologically pure microorganism, naturally occurring microorganism, non-naturally occurring microorganism, non-naturally occurring microorganism produced by genetic modification, mutant of naturally occurring microorganism, mutant of non-naturally occurring microorganism, recombinant microorganism, engineered microorganism, artificially synthesized microorganism; wherein said microorganism comprises selection from *Acetogenium kivui*, *Acetobacterium woodii*, *Acetoanaerobium noterae*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum*, *Eubacterium limosum*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium ultunense*, *Clostridium ragsdali* P11 (ATCC BAA-622), *Alkalibaculum bacchi* CP11 (ATCC BAA-1772), *Clostridium coskatii*, *Clostridium carboxidivorans* P7 (ATCC PTA-7827), *Geobacter sulfurreducens*, *Morrella thermacetica*, *Peptostreptococcus productus*, *Clostridium drakei*, recombinant microorganism (DSM 24138), and mixtures thereof; wherein said microorganism comprises one or more strains of *Clostridium ljungdahlii*, or one or more strains of *Clostridium ragsdalei*, or one or more strains of *Clostridium carboxidivorans*, or one or more strains of *Clostridium autoethanogenum*; wherein said microorganism comprises one or more genetically modified microorganism produced by inserting one or more selected genes into host organism selected from any *Clostridium ljungdahlii* strains, or any *Clostridium ragsdalei* strains, or any *Clostridium carboxidivorans* strains, or any *Clostridium autoethanogenum* strains; wherein said microorganism comprises one or more genetically modified microorganism produced by inserting into any host organism one or more genes from any *Clostridium ljungdahlii* strain, or any *Clostridium ragsdalei* strain, or any *Clostridium carboxidivorans* strain, or any *Clostridium autoethanogenum* strain.

As an embodiment, the present disclosure provides said bioreactor comprising one or more reactors; wherein said bioreactor comprising cell recycle; wherein adding flow of nutrient medium into bioreactor.

DESCRIPTION OF FIGURES

FIG. 1 comprises a schematic diagram illustrating an embodiment of the process of microbial fermentation of a gaseous substrate.

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions of sustaining microorganism culture, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about."

The term "acetogen" or "acetogenic" refers to a bacterium that generates acetate as a product of anaerobic respiration. This process is different from acetate fermentation, although both occur in the absence of oxygen and produce acetate. These organisms are also referred to as acetogenic bacteria, since all known acetogens are bacteria. Acetogens are found in a variety of habitats, generally those that are anaerobic (lack oxygen). Acetogens can use a variety of compounds as sources of energy and carbon; the best studied form of acetogenic metabolism involves the use of carbon dioxide as a carbon source and hydrogen as an energy source.

The terms "bioreactor," "reactor," or "fermentation bioreactor," include a fermentation device consisting of one or more vessels and/or towers or piping arrangement, which includes the Continuous Stirred Tank Reactor (CSTR), Bubble Column, Gas lift Fermenter, Static Mixer, or other device suitable for gas-liquid contact. For the method of this disclosure, the fermentation bioreactor may comprise a growth reactor which feeds the fermentation broth to a second fermentation bioreactor, in which most of the product, ethanol, is produced.

The term "conversion" means a fraction of input quantity that is converted into product(s); this is denoted in the following equation: (input quantity−output quantity)/(input quantity).

The term "fermentation" means fermentation of CO to alcohols and acetate. A number of bacteria are known to be capable of carrying out the fermentation of CO to alcohols, including butanol and ethanol, and acetic acid, and are suitable for use in the process of the present disclosure. Examples of such bacteria that are suitable for use in the disclosure include those of the genus *Clostridium*, such as strains of *Clostridium ljungdahlii*, including those described in WO 2000/68407, EP 117309, U.S. Pat. Nos. 5,173,429, 5,593,886, and 6,368,819, WO 1998/00558 and WO 2002/08438, strains of *Clostridium autoethanogenum* (DSM 10061 and DSM 19630 of DSMZ, Germany) including those described in WO 2007/117157 & WO 2009/151342 and *Clostridium ragsdalei* (P11, ATCC BAA-622) including those described respectively in U.S. Pat. No. 7,704,723 and "Biofuels and Bioproducts from Biomass-Generated Synthesis Gas," Hasan Atiyeh, presented in Oklahoma EPSCoR Annual State Conference, Apr. 29, 2010 and *Clostridium carboxidivorans* (ATCC BAA-624) described in US Patent Application No. 20070275447. Other suitable bacteria include those of the genus *Moorella*, including *Moorella* sp HUC22-1, and those of the genus *Carboxydothermus*. The disclosures of each of these publications are fully incorporated herein by reference. In addition, other bacteria may be selected for use in the process of the disclosure by a person of skill in the art. It will also be appreciated that a mixed culture of two or more bacteria may be used in the process of the present disclosure. One microorganism suitable for use in the present disclosure is *Clostridium autoethanogenum*. Fermentation may be carried out in any suitable bioreactor, such as a continuous stirred tank reactor (CTSR), a bubble column reactor (BCR) or a trickle bed reactor (TBR). Also, in some preferred embodiments of the disclosure, the bioreactor may comprise a first, growth reactor in which the microorganisms are cultured, and a second, fermentation reactor, to which fermentation broth from the growth reactor is fed and in which most of the fermentation product (ethanol and acetate) is produced.

The term "fermentation broth" means: the composition of the fermentation medium comprises anything that ends up in the fermentation broth including: raw substrates, fermentation products, microorganism(s) and derived components, chemical additives, nutrients, gases. All three main phases; solid, liquid and gases are present in the fermentation broth and their possible interactions The term "flow factor" means proposed quantity of gaseous feed divided by current quantity of gaseous feed.

The term "microorganism" or "microbe" includes bacteria, fungi, yeast, archaea, and protists; microscopic plants (called green algae); and animals such as plankton, the planarian and the amoeba. Some also include viruses, but others consider these as non-living. Microorganisms live in all parts of the biosphere where there is liquid water, including soil, hot springs, on the ocean floor, high in the atmosphere and deep inside rocks within the Earth's crust. Microorganisms are critical to nutrient recycling in ecosystems as they act as decomposers. Microbes are also exploited by people in biotechnology, both in traditional food and beverage preparation, and in modern technologies based on genetic engineering. It is envisioned that mixed strain microorganisms, that may or may not contain strains of various microorganisms, will be utilized in the present disclosure. Also, it is envisioned that directed evolution can selectively screen microorganisms that can be utilized in the present disclosure. It is further envisioned that recombinant DNA technology can create microorganisms using select strains of existing microorganisms. Also chemical mutagenesis technology (mutating bacterial DNA using various chemicals) can create microorganisms using select strains of existing microorganisms. It is envisioned that bacteria which are able to convert CO and water or $H_2$ and $CO_2$ into ethanol and acetic acid products will be utilized in the present disclosure. Some examples of useful bacteria include *Acetogenium kivui, Acetobacterium woodii, Acetoanaerobium noterae, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum, Eubacterium limosum, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium ultunense, Clostridium ragsdali* P11 (ATCC BAA-622), *Alkalibaculum bacchi* CP11 (ATCC BAA-1772), *Clostridium coskatii, Clostridium carboxidivorans* P7 (ATCC PTA-7827), *Geobacter sulfurreducens, Morrella thermacetica, Peptostreptococcus productus, Clostridium drakei*, recombinant microorganism (DSM 24138), and mixtures thereof.

The term "nutrient medium" comprises microorganism growth medium which may contain one or more of vitamins and minerals that permit growth of selected microorganism. Components of a variety of nutrient media suitable to the use of this invention are known and reported in prior publications such as International Patent Application No. WO 2008/00558, U.S. Pat. Nos. 7,285,402, 5,807,722; 5,593,886, and 5,821,111.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is also used as intermediate in producing synthetic petroleum for use as a fuel or lubricant via Fischer-Tropsch synthesis and previously the Mobil methanol to gasoline process. Syngas consists primarily of hydrogen, carbon monoxide, and very often some carbon dioxide.

DETAILED DESCRIPTION

The present disclosure provides a method of gaseous substrate fermentation comprising: adding gaseous substrate comprising carbon monoxide (CO) and hydrogen ($H_2$) into an aqueous medium in a bioreactor; said aqueous medium comprising one or more microorganism; said method comprising measuring conversion of CO; measuring conversion of $H_2$; increasing flow of gaseous substrate by a preselected flow factor in 1.0 to 2.0 range; wherein agitation comprises greater than or equal to target agitation rate; wherein said target agitation rate comprises an agitator speed of 10 to 1000 rpm.

The present disclosure provides a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganism; said method comprising measuring conversion of CO; measuring conversion of $H_2$; increasing flow of gaseous substrate by a preselected flow factor in 1.0 to 2.0 range; wherein speed of said agitator comprises greater than or equal to target speed in 10 to 1000 rpm range.

As an embodiment, means of agitation or means of agitating can be accomplished by mechanical agitator, mechanical stirrer, liquid recirculation, liquid pump-around, liquid injection, gas injection, etc.

As an embodiment, the method of the present disclosure comprises increasing flow of gaseous substrate wherein said conversion of CO exceeds a first CO conversion in 25% to 95% range.

As an embodiment, the method of the present disclosure comprises increasing flow of gaseous substrate wherein conversion of $H_2$ exceeds a first $H_2$ conversion in 25 to 95% range.

Further, the present disclosure provides a method of gaseous substrate fermentation comprising: adding gaseous substrate comprising carbon monoxide (CO) and hydrogen ($H_2$) into an aqueous medium in a bioreactor; said aqueous medium comprising one or more microorganism; said method comprising measuring conversion of CO; measuring conversion of $H_2$; increasing flow of gaseous substrate by a preselected flow factor in 1.0 to 2.0 range; wherein difference between conversion of CO and conversion of $H_2$ comprises greater than or equal to a specified conversion difference in 0% to 25% range.

Further, the present disclosure provides, a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganism; said method comprising measuring conversion of CO; measuring conversion of $H_2$; increasing flow of gaseous substrate by a preselected flow factor in 1.0 to 2.0 range; wherein difference between conversion of CO and conversion of $H_2$ comprises greater than or equal to a specified conversion difference in 0% to 25% range.

As an embodiment, the method of the present disclosure comprises increasing flow of gaseous substrate wherein conversion of CO exceeds a first CO conversion in 25 to 95% range.

As an embodiment, the method of the present disclosure comprises increasing flow of gaseous substrate wherein conversion of $H_2$ exceeds a first $H_2$ conversion in 25 to 95% range.

Also, the present disclosure provides a method of gaseous substrate fermentation comprising: adding gaseous substrate comprising carbon monoxide (CO) and hydrogen ($H_2$) into an aqueous medium in a bioreactor comprising agitation; said aqueous medium comprising one or more microorganisms; said method comprising measuring conversions of CO and $H_2$ and increasing agitation in preselected speed steps; wherein difference of conversions of CO and $H_2$ is less than a specified conversion difference in a range of 0 to 25%; comprising increasing agitation wherein conversion of CO exceeds a second CO conversion in a range of 0 to 25%; comprising increasing agitation wherein conversion of $H_2$ exceeds a second $H_2$ conversion in a range of 0 to 25%.

Also, the present disclosure provides, a method of gaseous substrate fermentation comprising: adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing speed of said agitator in preselected speed steps in a range of 0 to 200 rpm; wherein difference of conversions of CO and $H_2$ is less than a specified conversion difference in a range of 0 to 25%.

As an embodiment, the method of the present disclosure comprises increasing speed of said agitator wherein conversion of CO exceeds a second CO conversion in a range of 0 to 25%.

As an embodiment, the method of the present disclosure comprises increasing speed of said agitator wherein conversion of $H_2$ exceeds a second $H_2$ conversion in a range of 0 to 25%.

As an embodiment, said microorganism of the present disclosure comprises one or more of biologically pure anaerobic acetogenic bacteria; wherein said microorganism comprises one or more of naturally occurring anaerobic acetogenic bacteria; wherein said microorganism comprises one or more of non-naturally occurring anaerobic acetogenic bacteria; wherein said microorganism comprises one or more of non-naturally occurring anaerobic acetogenic bacteria produced by genetic modification using anaerobic acetogenic bacteria as host organism; wherein said microorganism comprises one or more of non-naturally occurring anaerobic acetogenic bacteria produced by inserting genes of anaerobic acetogenic bacteria into a host organism; wherein said microorganism selection from some examples of useful bacteria include *Acetogenium kivui*, *Acetobacterium woodii*, *Acetoanaerobium noterae*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum*, *Eubacterium limosum*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* 0-52 (ATCC 55889), *Clostridium ultunense*, *Clostridium ragsdali* P11 (ATCC BAA-622), *Alkalibaculum bacchi* CP11 (ATCC BAA-1772), *Clostridium coskatii*, *Clostridium carboxidivorans* P7 (ATCC PTA-7827), *Geobacter sulfurreducens*, *Morrella thermacetica*, *Peptostreptococcus productus*, *Clostridium drakei*, recombinant microorganism (DSM 24138), and mixtures thereof; wherein said microorganism comprises one or more strains of *Clostridium ljungdahlii*, or one or more strains of *Clostridium ragsdalei*, or one or more strains of *Clostridium carboxidivorans*, or one or more strains of *Clostridium autoethanogenum*; wherein said microorganism comprises one or more genetically modified microorganism produced by inserting one or more selected genes into host organism selected from any *Clostridium ljungdahlii* strains, or any *Clostridium ragsdalei* strains, or any *Clostridium carboxidivorans* strains, or any *Clostridium autoethanogenum* strains; wherein said microorganism comprises one or more genetically modified microorganism produced by inserting into any host organism one or more genes from any *Clostridium ljungdahlii* strain, or any *Clostridium ragsdalei* strain, or any *Clostridium carboxidivorans* strain, or any *Clostridium autoethanogenum* strain.

As an embodiment, the present disclosure provides said bioreactor comprising one or more reactors; wherein said bioreactor comprising cell recycle; wherein adding flow of nutrient medium into bioreactor.

FIG. 1 presents a process for the production of chemical, such as alcohol product mixture, from a gaseous substrate comprising carbon monoxide (CO), such as syngas by fermentation with bacteria, wherein the process comprises a bioreactor (100) containing fermentation broth comprising said bacteria cells and a fermentation medium. A gaseous stream comprising gaseous substrate comprising CO (101) can be fed into the bioreactor along with a stream of fermentation medium (102). A stream of fermentation broth (110) comprising said bacteria cells and said product chemical(s) can be removed from said bioreactor. A stream of fermentor off-gas (120) comprising unused portion of said gaseous stream comprising gaseous substrate is vented from the bioreactor. In one embodiment the stream of fermentor broth (110) flows to a cell recycle apparatus (200) wherein the cells are concentrated and returned (220) to the bioreactor. A permeate stream (210) from said cell recycle apparatus is directed to process of recovery of said chemical(s) (not shown on diagram). In one embodiment the stream of fermentor broth (110) is directed to process of recovery of said alcohol product mixture (not shown on diagram).

In one embodiment, the bioreactor (100) is equipped with an agitator (105) to provide agitation in order to facilitate contact of gaseous stream comprising gaseous substrate and enhance mass transfer of gaseous substrate with liquid fermentation medium. It is desirable to have good mass transfer rate and thus adequate agitation in the bioreactor throughout the fermentation process.

There are arrangements for collecting samples of gaseous stream comprising gaseous substrate introduced into bioreactor (101) and off-gas leaving bioreactor (120) (not shown in FIG. 1). There is arrangement for collecting samples of fermentation broth of bioreactor (not shown in FIG. 1). Said gas and liquid samples are collected at intervals and analyzed for consumption or production of various gas components, production of various products and the optical density of the fermentation broth.

These measured values can be used to calculate specific carbon monoxide (CO) uptake (SCU) and cell density in fermentation broth in the bioreactor using following equations:

$$\text{CO uptake, mmol/min} = (\text{mmol/min CO input}) - (\text{mmol/min CO output}) \quad (1)$$

$$\text{Cell density, g/L} = (\text{Optical density}) \cdot (\text{Dilution factor}) \cdot (\text{Cell mass constant}) \quad (2)$$

$$\text{Cell mass, g} = (\text{Cell density}) \cdot (\text{Volume of bioreactor}) \quad (3)$$

$$\text{Specific CO uptake, mmol/min/g} = (\text{CO uptake})/(\text{Cell mass}) \quad (4)$$

Cell density is mass of cell per unit volume of fermentor broth. Volume of bioreactor is liquid volume in the bioreactor when agitation is turned off. Cell mass constant is mass (g) of dry bacteria cells per liter fermentation broth with optical density of one (1). Optical density in equation two (2) is the measured optical density of a sample obtained after dilution of fermentor broth with a suitable solvent such as saline.

Microorganism used in the method of this disclosure may comprise one or more of biologically pure anaerobic acetogenic bacteria.

Microorganism used in the method of this disclosure: may comprise one or more of naturally occurring anaerobic acetogenic bacteria; may comprise one or more of non-naturally occurring anaerobic acetogenic bacteria; may comprise one or more of non-naturally occurring anaerobic acetogenic bacteria produced by genetic modification using anaerobic acetogenic bacteria as host organism; may comprise one or more of non-naturally occurring anaerobic acetogenic bacteria produced by inserting genes of anaerobic acetogenic bacteria into a host organism.

Microorganism used in the method of this disclosure may comprise one or more bacteria selected from *Acetogenium kivui*, *Acetobacterium woodii*, *Acetoanaerobium noterae*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium autoethanogenum* (DSM 23693), *Clostridium autoethanogenum* (DSM 19630 of DSMZ Germany), *Clostridium autoethanogenum* (DSM 10061 of DSMZ Germany), *Clostridium thermoaceticum*, *Eubacterium limosum*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* 0-52 (ATCC 55889), *Clostridium ultunense*, *Clostridium ragsdali* P11 (ATCC BAA-622), *Alkalibaculum bacchi* CP11 (ATCC BAA-1772), *Clostridium coskatii*, *Clostridium carboxidivorans* P7 (ATCC PTA-7827), *Geobacter sulfurreducens*, *Morrella thermacetica*, *Peptostreptococcus productus*, *Clostridium drakei*, recombinant microorganism (DSM 24138), and mixtures thereof.

In one embodiment, microorganism used in the method of this disclosure comprises one or more strains of *Clostridium ljungdahlii*, or one or more strains of *Clostridium ragsdalei*, or one or more strains of *Clostridium carboxidivorans*, or one or more strains of *Clostridium autoethanogenum*.

In one embodiment, microorganism used in the method of this disclosure comprises one or more genetically modified microorganism produced by inserting one or more selected genes into host organism selected from any *Clostridium ljungdahlii* strains, or any *Clostridium ragsdalei* strains, or any *Clostridium carboxidivorans* strains, or any *Clostridium autoethanogenum* strains.

In one embodiment, microorganism used in the method of this disclosure comprises one or more genetically modified microorganism produced by inserting into any host organism one or more genes from any *Clostridium ljungdahlii* strain, or any *Clostridium ragsdalei* strain, or any *Clostridium carboxidivorans* strain, or any *Clostridium autoethanogenum* strain.

One embodiment of the method of the present disclosure comprises: adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing speed of said agitator in preselected speed steps in a range of 0 to 200 rpm; wherein difference of conversions of CO and $H_2$ is less than a specified conversion difference in a range of 0 to 25%. In one embodiment conversion of CO exceeds a first CO conversion in a range of 0 to 25%. In one embodiment conversion of $H_2$ exceeds a first $H_2$ conversion in a range of 0 to 25%. Actions of measuring conversions of CO and $H_2$ and increasing speed of said agitator may be repeated. In one embodiment CO conversion is greater than $H_2$ conversion. In one embodiment CO conversion is less than $H_2$ conversion. In one embodiment agitation speed is increased by a smaller magnitude if the current agitation speed is low and by a bigger magnitude if the current agitation speed is high. In one embodiment agitation speed is increased by a smaller magnitude if the current CO and $H_2$ conversions are low and by a bigger magnitude if the current CO and $H_2$ conversions are high. For example in one embodiment in a range of 200 to 400 rpm agitation speed, if CO and $H_2$ conversions are respectively in ranges of 20 to 30% and 10 to 15% and numerically within 15% of each other, agitation speed is increased by about 50 rpm. In a range of 400 to 600 rpm agitation speed, if CO and $H_2$ conversions are respectively in ranges of 30 to 50% and 15 to 35% and numerically within 15% of each other, agitation speed is increased by 100 rpm.

One embodiment of the method of the present disclosure comprises adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing flow of gaseous substrate by a preselected flow factor in a range of 1.0 to 2.0 of current value; wherein difference of conversions of CO and $H_2$ is less than or equal to a specified conversion difference in a range of 0 to 25%. In one embodiment conversion of CO exceeds a first CO conversion in a range of 0 to 25%. In one embodiment conversion of $H_2$ exceeds a first $H_2$ conversion in a range of 0 to 25%.

In one embodiment, flow rate of gaseous substrate is increased between two consecutive increases in agitator speed. In one embodiment, flow rate of gaseous substrate is increased between every two consecutive increases in agitator speed. In one embodiment, flow rate of gaseous substrate is increased between alternate two increases in agitator speed.

One embodiment of the method of the present disclosure comprises adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing flow of gaseous substrate by a preselected flow factor in a range of 1.0 to 2.0 of current value; wherein difference of conversions of CO and $H_2$ is greater than or equal to a specified conversion difference in a range of 0 to 25%. In one embodiment conversion of CO exceeds a second CO conversion in a range of 25 to 95%. In one embodiment conversion of $H_2$ exceeds a second $H_2$ conversion in a range of 25 to 95%.

One embodiment of the method of this disclosure comprises adding gaseous substrate comprising carbon monoxide (CO) and hydrogen ($H_2$) into an aqueous medium in a bioreactor comprising an agitator; said aqueous medium comprising one or more microorganisms; said method comprising measuring conversions of CO and $H_2$ and increasing flow of gaseous substrate by a preselected flow factor in a range of 1.0 to 2.0 of current value; wherein speed of agitator is greater than or equal to a target speed in a range of 10 to 1000 rpm. In one embodiment conversion of CO exceeds a second CO conversion in a range of 25 to 95%. In one embodiment conversion of $H_2$ exceeds a second $H_2$ conversion in a range of 25 to 95%. The actions of measuring conversions of CO and $H_2$ and increasing flow of gaseous substrate by a preselected flow factor may be repeated. Value of preselected flow factor can be different in different repeats. In one embodiment a low value of flow factor is used wherein $H_2$ conversion is low and a high value of flow factor is used wherein $H_2$ conversion is high. For example in one embodiment, a flow factor in a range of 1.00 to 1.05 may be used wherein $H_2$ conversion is greater than 45%; a flow factor in a range of 1.05 to 1.10 may be used wherein $H_2$ conversion is greater than 50%; a flow factor in a range of 1.10 to 1.15 may be used wherein $H_2$ conversion is greater than 65%; a flow factor in a range of 1.15 to 1.20 may be used wherein $H_2$ conversion is greater than 75%.

Typically in a laboratory scale bioreactor such as New Brunswick Bioflow I bioreactor, agitator speed in the range of 300-900 revolutions per minute (rpm) provides adequate agitation for desirable mass transfer rate. In one embodiment, agitator speed in the range of 500-700 rpm is used. In one embodiment, agitator speed in the range of 550-650 rpm is used. In one embodiment, agitator speed of about 600 rpm is used.

In an embodiment, for a larger scale bioreactor such as a bioreactor of about 100 to 500 liter size, agitator speed in the range of about 50 to about 500 rpm is used for agitation. In an embodiment, for a commercial scale bioreactor of about 100,000 to about 1000,000 liter size, agitator speed in the range of about 1 to about 50 rpm is used for agitation. In various embodiments, a larger bioreactor requires smaller rpm compared to a smaller bioreactor.

As an embodiment, the present disclosure provides temperature control in the bioreactor in the range of 25 to 50° C.

In one embodiment of the method of the present disclosure, said bioreactor comprises one reactor. In one embodiment of the method of the present disclosure, said bioreactor comprises two or more reactors.

In one embodiment of the method of the present disclosure, said bioreactor comprises cell recycle unit.

In one embodiment of the method of the present disclosure, said gaseous stream comprising gaseous substrate comprising CO also comprises hydrogen. In one embodiment, said gaseous stream comprising gaseous substrate comprising CO comprises syngas. In one embodiment, said gaseous stream comprising gaseous substrate comprising CO comprises steel mill off-gas. In one embodiment, said gaseous stream comprising gaseous substrate comprising CO comprises syngas obtained by gasification of carbonaceous material comprising biomass.

In one embodiment one or more growth or seed fermentors provide the initial supply of inoculum of bacteria cells. In one embodiment one or more growth or seed fermentors continue to supply bacteria cells to bioreactor in conjunction with the method of this disclosure. In one embodiment of the present disclosure, the process comprises cell recycle.

Nutrient medium comprises microorganism growth medium which may contain one or more of vitamins and minerals that permit growth of selected microorganism. Table 1 provides an embodiment of nutrient medium as contemplated by the present disclosure. Other nutrient medium suitable for the present disclosure is known in the art. Moreover, nutrient medium that is not disclosed in the art but derived from various components described in Table 1 can be utilized by the present invention. The present disclosure provides for improved compositions of nutrient medium.

TABLE 1

Medium Component and Their Concentrations

| Component/Ion | Added As | Conc in ppm |
|---|---|---|
| $NH_4^+$ | $NH_4Cl/(NH_4)_2HPO_4$ | ≤838 |
| Fe | $FeCl_2 \cdot 4H_2O$ | ≤17 |
| Ni | $NiCl_2 \cdot 6H_2O$ | ≤0.2 |
| Co | $CoCl_2 \cdot 6H_2O$ | ≤1.0 |
| Se | $Na_2SeO_3$ | ≤0.1 |
| Zn | $ZnSO_4 \cdot 7H_2O$ | ≤0.5 |
| Mo | $Na_2MoO_4 \cdot 2H_2O$ | ≤0.3 |
| Mn | $MnCl_2 \cdot 4H_2O$ | ≤0.2 |
| B | $H_3BO_3$ | ≤1.1 |
| Cu | $CuCl_2 \cdot 2H_2O$ | ≤0.15 |
| W | $Na_2WO_4 \cdot 2H_2O$ | ≤1.2 |
| K | KCl | ≤79 |
| Mg | $MgCl_2 \cdot 6H_2O$ | ≤60 |

TABLE 1-continued

Medium Component and Their Concentrations

| Component/Ion | Added As | Conc in ppm |
|---|---|---|
| Na | NaCl | ≤80* |
| Ca | $CaCl_2 \cdot 2H_2O$ | ≤55 |
| Cysteine HCl | Cysteine HCl | ≤250 |
| $PO_4^{-2}$ | $H_3PO_4/(NH_4)_2HPO_4$ | ≤820 |
| Pantothenic Acid | Pantothenic Acid | ≤0.04 |
| Biotin | Biotin | ≤0.02 |
| Thiamin | Thiamine | ≤0.05 |

*$Na^+$ concentration is from NaCl only. It does not include $Na^+$ from the other components such as $Na_2WO_4 \cdot 2H_2O$.
** $Ca^{+2}$ concentration does not include calcium from pantothenic acid, calcium salt (i.e. Calcium d-Pantothenate).

EXAMPLES

Comparative Example (See Example 11 in U.S. Pat. No. 7,285,402)

To prepare the stock cultures for inoculation of the reactor, cultures of *Clostridium ljungdahlii*, strain C-01 (ATCC Accession No. 55988) were grown up in 150 mL serum bottles on CO, $CO_2$ and $H_2$ in a rich medium containing 1 g/L yeast extract and 1 g/L trypticase, in salts and vitamins. The vitamin concentration employed was 0.4 mL/L medium of an aqueous solution containing 50.5 mg/L calcium pantothenate, 20.6 mg/L d-biotin and 50.6 mg/L thiamine HCl. Bottles were incubated at 37° C. in a shaker incubator. The cultures were grown to the exponential growth phase, as determined by visual inspection. With each inoculation, approximately 90 mL of stock culture were transferred from serum bottles to 1 liter of medium, representing 9% by volume inoculation. A successful inoculation is described below. The outlined procedure can be repeated several times to obtain a successful inoculation.

In obtaining a successful inoculation, 90 mL/L of inoculum were added to a 1 liter batch of basal medium containing 0.4 mL/L vitamins and salts (t=0). The agitation rate was 240 rpm, the pH was 5.3, the temperature was 38.5° C. and the gas retention time (continuous gas flow) was 110 minutes. The gas feed contained 62% $H_2$, 31% CO and 7% $C_2H_6$. After 13 hr (t=13 hr) some CO conversion was noted, and at t=23 hr the agitation rate was increased from 240 rpm to 300 rpm. The gas retention time was decreased to 100 minutes at t=27 hr, and a further decrease in gas retention time was made at t=46 hr. The agitation rate was also increased in 100 rpm increments at t=28 hr, 59 hr, 72 hr and 85 hr.

By t=110 hr, the system was operating with a gas retention time of 80 minutes and an agitation rate of 600 rpm. The cell concentration was 0.5 g/L and the CO conversion was 35%. There was still no $H_2$ conversion, but small amounts of ethanol and acetate (about .1 g/L each) had accumulated in the batch culture broth. The efforts up until this time emphasized cell growth in the reactor.

Medium flow using the same concentrations as in basal medium was started at a rate of 0.4 mL/min at t=120 hr. A program of nominal increases in gas rate, agitation rate and medium rate was then initiated while carefully maintaining the system under excess $H_2$. By t=210 hr, the ethanol concentration was 17 g/L, the acetate concentration was 1 g/L, the cell concentration was 1.6 g/L, the CO conversion was nearly 100% and the $H_2$ conversion was 90%. The ethanol productivity reached 11.4 g/L-day.

A program of gradual gas rate increases was again started. Concurrent vitamin increases were made to bring the vitamin addition rate to 0.7 mL/L medium. By t=610 hr, the reactor was producing 20 g/L ethanol and about 2 g/L acetate. The CO conversion was nearly 100% and the $H_2$ conversion was 85%. The ethanol productivity reached 14 g/L.day.

Fermentation Medium for examples 1-4 comprise one or more components selected from those presented in Table 1.

Example 1

*Clostridium ljungdahalii* PETC: Increasing the Cell Density of Bacteria in the Reactor by Maintaining CO and $H_2$ Conversion Difference at a Predetermined Value New Brunswick bioflow I reactor containing fermentation medium was started with 0.45 g/L of actively growing *Clostridium ljungdahalii*. Before the start of the experiment the rate of agitation of the reactor was set to 100 rpm and the rate of flow of gas was set to 25 mL/min. Gas and liquid samples taken from the reactor at every 2 to 4 hour intervals were analyzed for consumption or production of various gas components, broth acetic acid concentration, broth ethanol concentration and the optical density of the culture. The syngas flow to the reactor was measured real time. Agitation of the reactor was increased in a stepwise fashion based on the conversions of CO and $H_2$. The criteria used to increase agitation were as follows; in the range of 100 to 500 rpm if CO and $H_2$ conversions were >10% and numerically within 15% of each other, i.e. $H_2$ was 12% and CO was 25%, agitation was increased by 50 rpm. In the range of 500 to 600 rpm: If CO and $H_2$ conversions were numerically within 15% of each other, i.e. $H_2$ was 30% and CO was 43%, agitation was increased by 100 rpm. Similarly the rate of flow of gas to the reactor was increased in a stepwise fashion. The criteria used to increase gas were as follows:

If $H_2$ conversion was >45% gas was increased by 5%
If $H_2$ conversion was >50% gas was increased by 10%
If $H_2$ conversion was >65% gas was increased by 15%
If $H_2$ conversion was >75% gas was increased by 20%

In all the above scenarios gas was increased only if the CO conversion was more than 65%.

After bacteria started growing actively in the reactor (when the cell density of the reactor reach about 50% more than the initial cell density) culture was supplemented with composition of vitamins (in addition to the vitamins already in the medium) if the acetic acid concentration of the culture broth is below a predetermined value. Criteria used to add cocktail of vitamins to the culture was as follow as: if the culture broth acetic acid is less than about 2.5 g/L, about 0.34 mL of vitamins per liter of culture was added, if the culture broth acetic acid is less than about 2 g/L, about 0.67 mL of vitamins per liter of culture was added, if the culture broth acetic acid is less than about 1.5 g/L, about 1 mL of vitamins per liter was added. Composition of vitamins used in these experiments were as follows:

| | |
|---|---|
| Biotin | 0.08-1 µM |
| Thiamin HCl | 0.12-1.5 µM |
| Calcium d-pantothenate | 0.15-2 µM |

ATCC vitamin supplement (catalog No. MD-VS) was added to PETC example to the final concentration of 1% (of fermentation medium) in addition to the Biotin, Thiamin and calcium pantothenate.

12.33 hours after the inoculation growth media flow to the reactor was started at 0.09 mL/min (approximate cell retention time: 277 hours). 16.08 hours after the inoculation growth media flow to the reactor was increased to 0.5 mL/min (approximate cell retention time: 50 hours). 17.8 hours after the inoculation a cell recycle system was attached to the reactor to control the high acetic acid (8.027 g/L) in the culture broth. At this point one seventh of culture (by volume) was used to purge the cell recycle system (as a result one seventh of the culture (by volume) was lost). Once the attachment of cell recycle system to the reactor was completed, at 18.02 hours after the inoculation, dilution of the broth acetic acid was started by increasing the growth media flow to 1.5 mL/min followed by drawing 1 mL/min permeate through the cell recycle system.

Cell density in the reactor was increased with time and reached the cell mass of 2 g/L within 93.13 hours after the inoculation of the reactor. At this point broth ethanol concentration of the culture was 3.8 g/L and the total broth acetic acid concentration was 6.93 g/L. During this start-up pH of the culture was maintained between 4.4 and 5.1. The temperature of the culture/reactor was maintained within 38.5 to 39.2° C.

Example 2

*Clostridium ljungdahlii* C-01: Increasing the Cell Density of Bacteria in the Reactor by Maintaining CO and $H_2$ Conversion Difference at a Predetermined Value New Brunswick Bioflow I bioreactor containing about 1.5 liter (e.g. in the range of about 1.32 to about 1.6 liters) of Fermentation Medium was started with about 0.28 g/L of actively growing *Clostridium ljungdahlii* C-01 strain. Prior to the start of the experiment rate of agitation in the bioreactor was set to about 100 rpm and the rate of flow of gas was set to about 30 mL/min. Temperature in the bioreactor was maintained in the range of about 36 to about 38° C. throughout the experiment. Samples of the following were taken and analyzed at different intervals (e.g. about 2 hour intervals): syngas feed into the bioreactor; off-gas from the bioreactor; fermentation broth in the bioreactor. The sample analysis provided: consumption of various gaseous components, production of various gaseous components, concentration of acetic acid, concentration of ethanol and optical density of the fermentation broth. First agitation of the reactor was increased from about 100 rpm in a stepwise fashion based on the conversion of CO and $H_2$. The criteria used to increase agitation were as follows: in the range of about 100 to about 500 rpm if CO and $H_2$ conversions were greater than or equal to about 10% and numerically within about 15% of each other, e.g. $H_2$ conversion was about 12% and CO conversion was about 25%, agitation was increased by about 50 rpm. In the range of about 500 to about 600 rpm: If CO and $H_2$ conversions were numerically within about 15% of each other, e.g. $H_2$ conversion was about 30% and CO conversion was about 43%, agitation was increased by about 100 rpm. Once the CO and $H_2$ conversions were equal to or greater than about 60% and about 45% respectively, rate of flow of gas to the reactor was increased in a stepwise fashion in addition to the agitation increases. The criteria used to increase gas were as follow:

If $H_2$ conversion was greater than or equal to about 45%, then syngas input was increased by about 5%;

If $H_2$ conversion was greater than or equal to about 50%, then syngas input was increased by about 10%;

If $H_2$ conversion was greater than or equal to about 65%, then syngas input was increased by about 15%;

If $H_2$ conversion was greater than or equal to about 75%, then syngas input was increased by about 20%.

After bacteria started growing actively in the reactor (when the cell density of the reactor reach about 50% more than the initial cell density) culture was supplemented with composition of vitamins (in addition to the vitamins already in the medium) if the acetic acid concentration of the culture broth is below a predetermined value. Criteria used to add cocktail of vitamins to the culture was as follow as: if the culture broth acetic acid is less than about 2.5 g/L, about 0.34 mL of vitamins per liter of culture was added, if the culture broth acetic acid is less than about 2 g/L, about 0.67 mL of vitamins per liter of culture was added, if the culture broth acetic acid is less than about 1.5 g/L, about 1 mL of vitamins per liter was added. Composition of vitamins used in these experiments were as follow:

| Biotin | 0.08-0.8 µM |
|---|---|
| Thiamin HCl | 0.12-1.2 µM |
| Calcium d-pantothenate | 0.15-1.5 µM |

About 28 hours after the inoculation media flow to the reactor was started at about 0.5 mL/min (approximate cell retention time: about 125 hours). All throughout the experiment pH was maintained around about 4.5.

Cell mass increased with time and reached the cell mass of about 2.8 g/L within about 128 hours after the inoculation of the reactor. At this point culture was producing more than about 25 g/L of ethanol.

Example 3

*Clostridium autoethanogenum* (DSM 10061): Increasing the Cell Density of Bacteria in the Reactor by Maintaining CO and $H_2$ Conversion Difference at a Predetermined Value New Brunswick Bioflow I bioreactor containing about 1.5 liter (e.g. in the range of about 1.38 to about 1.6 liters) of Fermentation Medium was started with about 0.33 g/L of actively growing *Clostridium autoethanogenum* strain. At the start of the experiment the rate of agitation in the bioreactor was set to 100 rpm and the rate of flow of gas was set to about 30 mL/min. Temperature in the bioreactor was maintained in the range of about 36 to about 37.5° C. throughout the experiment. Samples of the following were taken and analyzed at different intervals (e.g. about 2 hour intervals): syngas feed into the bioreactor; off-gas from the bioreactor; fermentation broth in the bioreactor. The sample analysis provided: consumption of various gaseous components, production of various gaseous components, concentration of acetic acid, concentration of ethanol and optical density of the fermentation broth. First agitation of the reactor was increased in a stepwise fashion based on the conversions of CO and $H_2$. The criteria used to increase agitation were as follows; in the range of about 100 to about 500 rpm if CO and $H_2$ conversions were greater than about 10% and numerically within about 15% of each other, e.g. $H_2$ conversion was about 12% and CO conversion was about 25%, agitation was increased by about 50 rpm. In the range of about 500 to about 600 rpm: If CO and $H_2$ conversions were numerically within about 15% of each other, e.g. $H_2$ was about 30% and CO was about 43%, agitation was increased by about 100 rpm. Once the CO and $H_2$ conversions were equal to or greater than about 65% and about 45% respectively the rate of flow of gas to the reactor was increased in a stepwise fashion in addition to the agitation increases. The criteria used to increase gas were as follows:

If $H_2$ conversion was greater than or equal to about 45%, then syngas input was increased by about 5%;

If $H_2$ conversion was greater than or equal to about 50%, then syngas input was increased by about 10%;

If $H_2$ conversion was greater than or equal to about 65%, then syngas input was increased by about 15%;

If $H_2$ conversion was greater than or equal to about 75%, then syngas input was increased by about 20%.

After bacteria started growing actively in the reactor (when the cell density of the reactor reach about 50% more than the initial cell density) culture was supplemented with composition of vitamins (in addition to the vitamins already in the medium) if the acetic acid concentration of the culture broth is below a predetermined value. Criteria used to add cocktail of vitamins to the culture was as follow as: if the culture broth acetic acid is less than about 2.5 g/L, about 0.34 mL of vitamins per liter of culture was added, if the culture broth acetic acid is less than about 2 g/L, about 0.67 mL of vitamins per liter of culture was added, if the culture broth acetic acid is less than about 1.5 g/L, about 1 mL of vitamins per liter was added. Composition of vitamins used in these experiments were as follows:

| Biotin | 0.08-0.8 µM |
|---|---|
| Thiamin HCl | 0.12-1.2 µM |
| Calcium d-pantothenate | 0.15-1.5 µM |

About 12.5 hours after the inoculation media flow to the reactor was started at about 0.1 mL/min (approximate cell retention time: about 233 hours). About 27.8 hours after the inoculation media flow to the reactor was started at about 0.2 mL/min (approximate cell retention time: about 116 hours). About 66.2 hours after the inoculation media flow to the reactor was started at about 0.42 mL/min (approximate cell retention time: about 61 hours). All through out the experiment pH was maintained around about 4.5.

Cell mass increased with time and reached the cell mass of about 2.59 g/L within about 120 hours after the inoculation of the reactor. At this point culture was producing more than about 19 g/L of ethanol.

Example 4

*Butyribacterium Methylotrophicum* (ATCC 33266)

Increasing the Cell Density of Bacteria in the Reactor by Maintaining CO and $H_2$ Conversion Difference at a Predetermined Value In this experiment, the start-up method of the present disclosure was tested with a non-clostridial acetogen.

This experiment was started in a New Brunswick bioflow I reactor containing 0.79 g/L of actively growing *Butyribacterium Methylotrophicum* in a fermentation medium as described above. Before the start of the experiment the rate of agitation of the reactor was set to 100 rpm and the rate of flow of gas was set to 40 mL/min. Gas and liquid samples taken from the reactor at every 2 to 4 hour intervals were analyzed for consumption or production of various gas components, broth acetic acid concentration, broth ethanol concentration and the optical density of the culture. Also, the composition of syngas was measured daily and the syngas flow to the reactor was measured real time by a mass flow controller regulating syngas to the reactor. Agitation of the reactor was increased in a stepwise fashion based on the conversions of CO and H2. The criteria used to increase agitation were as follows. In the range of 100 to 500 rpm if CO and H2 conversions were >10% and numerically within 15% of each other, i.e. H2 was 12% and CO was 25%, agitation was increased by 50 rpm. In the range of 500 to 600 rpm: If CO and H2 conversions were numerically within 15% of each other, i.e. H2 was 30% and CO was 43%, agitation was increased by 100 rpm. Similarly, the rate of flow of gas to the reactor was increased in a stepwise fashion. The criteria used to increase gas were as follows:

If H2 conversion was >45% gas was increased by 5%
If H2 conversion was >50% gas was increased by 10%
If H2 conversion was >65% gas was increased by 15%
If H2 conversion was >75% gas was increased by 20%

In all the above scenarios gas was increased only if the CO conversion was more than about 65%.

After bacteria started growing actively in the reactor (when the cell density of the reactor reach about 50% more than the initial cell density) culture was supplemented with composition of vitamins (in addition to the vitamins already in the medium) if the acetic acid concentration of the culture broth is below a predetermined value. Criteria used to add cocktail of vitamins to the culture was as follow as: if the culture broth acetic acid is less than about 2.5 g/L, about 0.34 mL of vitamins per liter of culture was added, if the culture broth acetic acid is less than about 2 g/L, about 0.67 mL of vitamins per liter of culture was added, if the culture broth acetic acid is less than about 1.5 g/L, about 1 mL of vitamins per liter was added. Composition of vitamins used in these experiments were as follows:

| Biotin | 0.08-0.8 µM |
|---|---|
| Thiamin HCl | 0.12-1.2 µM |
| Calcium d-pantothenate | 0.15-1.5 µM |

In this experiment a cell recycle system (CRS) was attached to the reactor before the start of the experiment. 09.58 hours after the start of the experiment fermentation medium (nutrient) flow to the reactor was started at a rate of 1 mL/min and through the CRS permeates at a rate of 1 mL/min was drawn out from the reactor.

Cell density in the reactor increased with time and reached the cell mass of 4.56 g/L within 43 hours after the inoculation of the reactor. At this point broth ethanol concentration of the culture was 10.53 g/L and the total broth acetic acid concentration was 4.24 g/L. During this start-up pH of the culture was maintained between 4.69 and 4.71. The temperature of the culture/reactor was maintained within 38.5 to 38.6° C.

Numerous modifications and variations of the present disclosure could be made by those skilled in the art without departing from the scope of the present disclosure included in the specific embodiments, examples, claims, application, etc., thereof. All published documents are incorporated by reference herein.

We claim:

1. A method of producing one or more alcohols from a gaseous substrate, the method comprising:
adding gaseous substrate comprising carbon monoxide (CO) and hydrogen ($H_2$) into an aqueous medium in a bioreactor, wherein the aqueous medium includes one or more anaerobic acetogenic microorganisms;
agitating the aqueous medium at an agitator speed of 10 to 1000 rpm;
measuring conversion of CO;
measuring conversion of $H_2$; and
increasing a flow rate of gaseous substrate into the bioreactor by a flow factor (proposed quantity of gaseous feed divided by current quantity of gaseous feed) of 1.05 to 2.0 when CO conversion in the bioreactor is 25 to 95%, $H_2$ conversion in the bioreactor is 25 to 95% and a difference between CO conversion and $H_2$ conversion in the bioreactor is 0% to 25%, wherein the agitator speed is increased when a second CO conversion is 0 to 25% and $H_2$ conversion is 0 to 25%
wherein if a concentration of acetic acid in the aqueous medium is less than about 2.5 grams per liter after reaching a cell density of at least 50% more than an initial cell density, then about 0.34 ml of a vitamin solution is added per liter of aqueous medium,
wherein the vitamin solution includes about 0.08 to about 1 µM biotin, about 0.12 to about 1.5 µM thiamin HCL, and about 0.15 to about 2 µM calcium d-pantothenate.

2. The method of claim 1 wherein the method includes adding a flow of nutrient medium into the bioreactor.

3. The method of claim 1 wherein the flow rate of gaseous substrates is increased between two consecutive increases in agitation speed.

4. The method of claim 1 wherein the flow rate of gaseous substrate is increased by 5% when $H_2$ conversion was greater than 45%.

5. The method of claim 1 wherein the flow rate of gaseous substrate is increased by 10% when $H_2$ conversion was greater than 50%.

6. The method of claim 1 wherein the flow rate of gaseous substrate is increased by 15% when $H_2$ conversion was greater than 65%.

7. The method of claim 1 wherein the flow rate of gaseous substrate is increased by 20% when $H_2$ conversion was greater than 75%.

8. A method of producing one or more alcohols from a gaseous substrate, the method comprising:
adding gaseous substrate comprising carbon monoxide (CO) and hydrogen ($H_2$) into an aqueous medium in a bioreactor, wherein the aqueous medium includes one or more anaerobic acetogenic microorganisms;
agitating the aqueous medium at an agitator speed of 10 to 1000 rpm;
measuring conversion of CO;
measuring conversion of $H_2$; and
increasing a flow rate of gaseous substrate into the bioreactor by a flow factor (proposed quantity of gaseous feed divided by current quantity of gaseous feed) of 1.05 to 2.0 when CO conversion in the bioreactor is 25 to 95%, $H_2$ conversion in the bioreactor is 25 to 95% and a difference between CO conversion and $H_2$ conversion in the bioreactor is 0% to 25%, wherein the agitator speed is increased when a second CO conversion is 0 to 25% and $H_2$ conversion is 0 to 25%
wherein if a concentration of acetic acid in the aqueous medium is less than about 2 grams per liter after reaching a cell density of at least 50% more than an initial cell density, then about 0.67 ml of a vitamin solution is added per liter of aqueous medium,
wherein the vitamin solution includes about 0.08 to about 1 µM biotin, about 0.12 to about 1.5 µM thiamin HCL, and about 0.15 to about 2 µM calcium d-pantothenate.

9. A method of producing, one or more alcohols from a gaseous substrate, the method comprising:
adding gaseous substrate comprising carbon monoxide (CO) and hydrogen ($H_2$) into an aqueous medium in a bioreactor, wherein the aqueous medium includes one or more anaerobic acetogenic microorganisms;

agitating the aqueous medium at an agitator speed of 10 to 1000 rpm;

measuring conversion of CO;

measuring conversion of $H_2$; and increasing a flow rate of gaseous substrate into the bioreactor by a flow factor (proposed quantity of gaseous feed divided by current quantity of gaseous feed) of 1.05 to 2.0 when CO conversion in the bioreactor is 25 to 95%, $H_2$ conversion in, the bioreactor is 25 to 95% and a difference between CO conversion and $H_2$ conversion in the bioreactor is 0% to 25%, wherein the agitator speed is increased when a second CO conversion is 0 to 25% and $H_2$ conversion is 0 to 25% wherein if a concentration of acetic acid in the aqueous medium is less than about 1.5 grams per liter after reaching a cell density of at least 50% more than an initial cell density, then about 1 ml of a vitamin solution is added per liter of aqueous medium, wherein the vitamin solution includes about 0.08 to about 1 µM biotin, about 0.12 to about 1.5 µM thiamin HCL, and about 0.15 to about 2 µM calcium d-pantothenate.

\* \* \* \* \*